(12) United States Patent
Begg (10) Patent No.: US 11,547,782 B2
(45) Date of Patent: Jan. 10, 2023

(54) FLUID COLLECTING SHEATHS FOR ENDOSCOPIC DEVICES AND SYSTEMS

(71) Applicant: Covidien LP, Mansfield, MA (US)

(72) Inventor: Nikolai D. Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 224 days.

(21) Appl. No.: 16/778,292

(22) Filed: Jan. 31, 2020

(65) Prior Publication Data

US 2021/0236702 A1 Aug. 5, 2021

(51) Int. Cl.
*A61M 1/00* (2006.01)
*A61B 34/35* (2016.01)
*A61B 34/00* (2016.01)

(52) U.S. Cl.
CPC ............ *A61M 1/0023* (2013.01); *A61M 1/90* (2021.05); *A61B 34/35* (2016.02); *A61B 34/71* (2016.02); *A61B 34/76* (2016.02); *A61M 2210/1433* (2013.01); *A61M 2210/1475* (2013.01)

(58) Field of Classification Search
CPC .................. A61M 1/0023; A61M 1/90; A61M 2210/1433; A61M 2210/1475; A61B 34/35; A61B 34/71; A61B 34/76; A61B 1/00128; A61B 1/0014; A61B 1/018; A61B 1/04; A61B 1/06; A61B 1/00137; A61B 1/015; A61B 1/303; A61B 1/00135
See application file for complete search history.

(56) References Cited

U.S. PATENT DOCUMENTS

| 1,585,934 A | 5/1926 | Muir |
| 1,666,332 A | 4/1928 | Hirsch |
| 1,831,786 A | 11/1931 | Duncan |

(Continued)

FOREIGN PATENT DOCUMENTS

| DE | 3339322 A1 | 5/1984 |
| DE | 3206381 C2 | 7/1986 |

(Continued)

OTHER PUBLICATIONS

Extended European Search Report issued in corresponding European Application No. 21153863.2 dated Jun. 29, 2021, 6 pages.

(Continued)

*Primary Examiner* — Benjamin J Klein
(74) *Attorney, Agent, or Firm* — Carter, DeLuca & Farrell LLP (57) ABSTRACT

A system includes an endoscope defining a proximal end, a distal end and an elongated shaft extending between the proximal end and the distal end of the endoscope. A fluid collecting sheath defines a proximal end and a distal end. The fluid collecting sheath is configured for insertion into a vaginal opening. The fluid collecting sheath includes fluid collecting apertures defined at the distal end of the fluid collecting sheath. A fluid line is in fluid communication with the fluid collecting apertures. A channel is formed in the fluid collecting sheath. The channel extends between the proximal end and the distal end of the fluid collecting sheath. The channel defines an opening therein. The channel of the fluid collecting sheath is configured to operably engage the elongated shaft of the endoscope by passing the elongated shaft of the endoscope through the opening of the channel.

20 Claims, 6 Drawing Sheets

(56) References Cited

U.S. PATENT DOCUMENTS

| | | |
|---|---|---|
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |

(56) References Cited

U.S. PATENT DOCUMENTS

| | | |
|---|---|---|
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,928,249 A | 7/1999 | Saadat et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 * | 11/2011 | Shener ............... A61B 1/015 600/159 |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,911,424 B2 * | 12/2014 | Weadock ........... A61M 25/0017 604/263 |
| 8,932,208 B2 | 1/2015 | Kendale et al. |
| 8,951,274 B2 * | 2/2015 | Adams ................ A61B 1/303 606/171 |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 * | 8/2015 | Sullivan ........... A61B 17/00234 |
| 9,125,550 B2 | 9/2015 | Shener-Irmakoglu et al. |
| 9,155,454 B2 * | 10/2015 | Sahney ............. A61B 1/00135 |
| 9,259,233 B2 | 2/2016 | Gruber et al. |
| RE47,285 E * | 3/2019 | Loske ............... A61B 1/00094 |
| 10,369,259 B2 * | 8/2019 | Kleiner ............... A61M 1/916 |
| 2007/0185380 A1 | 8/2007 | Kucklick |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0005750 A1 * | 1/2009 | West ................ A61M 25/00 604/385.03 |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0010299 A1 | 1/2010 | Bakos et al. |
| 2010/0010310 A1 * | 1/2010 | Weisenburgh, II .... A61B 1/126 600/156 |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2012/0123359 A1 * | 5/2012 | Reed ................ A61M 1/784 604/319 |
| 2013/0023840 A1 * | 1/2013 | Loske ................ A61B 90/39 604/319 |
| 2013/0131452 A1 | 5/2013 | Kuroda et al. |
| 2014/0003183 A1 | 1/2014 | Song |
| 2014/0005479 A1 * | 1/2014 | Loske ................ A61B 1/273 600/115 |
| 2017/0035949 A1 | 2/2017 | Loske |
| 2018/0132702 A1 | 5/2018 | Begg |
| 2018/0271354 A1 * | 9/2018 | Tilson ............... A61B 1/00082 |
| 2019/0246881 A1 | 8/2019 | Aull |
| 2020/0323422 A1 * | 10/2020 | Duan ................ A61B 1/015 |
| 2021/0186469 A1 * | 6/2021 | Johnsen ............. A61B 1/00094 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |

(56) References Cited

FOREIGN PATENT DOCUMENTS

| | | |
|---|---|---|
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |
| WO | 2016205126 A1 | 12/2016 |

OTHER PUBLICATIONS

European Examination Report issued in corresponding European Application No. 16736303.5 dated May 2, 2019, 5 pages.

* cited by examiner

FLUID COLLECTING SHEATHS FOR ENDOSCOPIC DEVICES AND SYSTEMS

BACKGROUND

Technical Field

The present disclosure relates to surgical instruments and, more particularly, to fluid collecting sheaths for endoscopic devices and systems.

Discussion of Related Art

Tissue resection may be performed endoscopically within an organ, such as a uterus, by inserting an endoscope (or hysteroscope) into the uterus and passing a tissue resection instrument through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

During a tissue resection procedure, for example, a pressure differential may cause fluid to leak out of the uterus through the opening through which the endoscope is inserted. Leaking fluid may travel down the length of the endoscope and drip onto the physician or the floor, presenting a hazard.

SUMMARY

In accordance with an aspect of the present disclosure, a system includes an endoscope defining a proximal end, a distal end and an elongated shaft extending between the proximal end and the distal end of the endoscope. A fluid collecting sheath defines a proximal end and a distal end. The fluid collecting sheath is configured for insertion into a vaginal opening. The fluid collecting sheath includes fluid collecting apertures defined at the distal end of the fluid collecting sheath. A fluid line is in fluid communication with the fluid collecting apertures. A channel is formed in the fluid collecting sheath. The channel extends between the proximal end and the distal end of the fluid collecting sheath. The channel defines an opening therein. The channel of the fluid collecting sheath is configured to operably engage the elongated shaft of the endoscope by passing the elongated shaft of the endoscope through the opening of the channel.

In some aspects, the channel of the fluid collecting sheath fixedly engages the elongated shaft of the endoscope. The fluid collecting sheath and the endo scope move in concert with one another.

In some aspects, at least one drip flange is formed at the distal end of the fluid collecting sheath. The at least one drip flange directs fluid away from the channel of the fluid collecting sheath.

In some aspects, the system includes a collection vessel in fluid communication with the fluid line. The collection vessel receives fluid captured by the fluid collecting apertures.

In some aspects, a collar extends from the fluid line. The collar is configured to be secured to the endoscope. The collar may be at least partially elastic.

In some aspects, the fluid collecting sheath and the fluid line are a single integrally formed structure in which the fluid line extends within the fluid collecting sheath between the proximal end and the distal end of the fluid collecting sheath.

In some aspects, the opening of the channel is formed through an outer edge of the fluid collecting sheath.

In some aspects, the channel is configured to selectively expand in width.

In some aspects, the system includes a vacuum source in fluid communication with the fluid line. The vacuum source applies negative pressure to the fluid collecting apertures to draw fluid through the fluid line.

In some aspects, a single fluid collecting aperture may be defined at the distal end of the fluid collecting sheath.

BRIEF DESCRIPTION OF THE DRAWINGS

The accompanying drawings, which are incorporated in and constitute a part of this specification, illustrate aspects and features of the present disclosure and, together with the detailed description below, serve to further explain the present disclosure, in which.

DETAILED DESCRIPTION

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Descriptions of technical features or aspects of an exemplary endoscopic system of the present disclosure should typically be considered as available and applicable to other similar features or aspects in another exemplary endoscopic system of the present disclosure. Accordingly, technical features described herein according to one exemplary endoscopic system of the present disclosure may be applicable to other exemplary endoscopic systems of the present disclosure, and thus duplicative descriptions may be omitted herein.

Exemplary endoscopic systems of the present disclosure will be described more fully below (e.g., with reference to the accompanying drawings). Like reference numerals may refer to like elements throughout the specification and drawings.

The endoscope described herein may be a hysteroscope.

Figure 1:
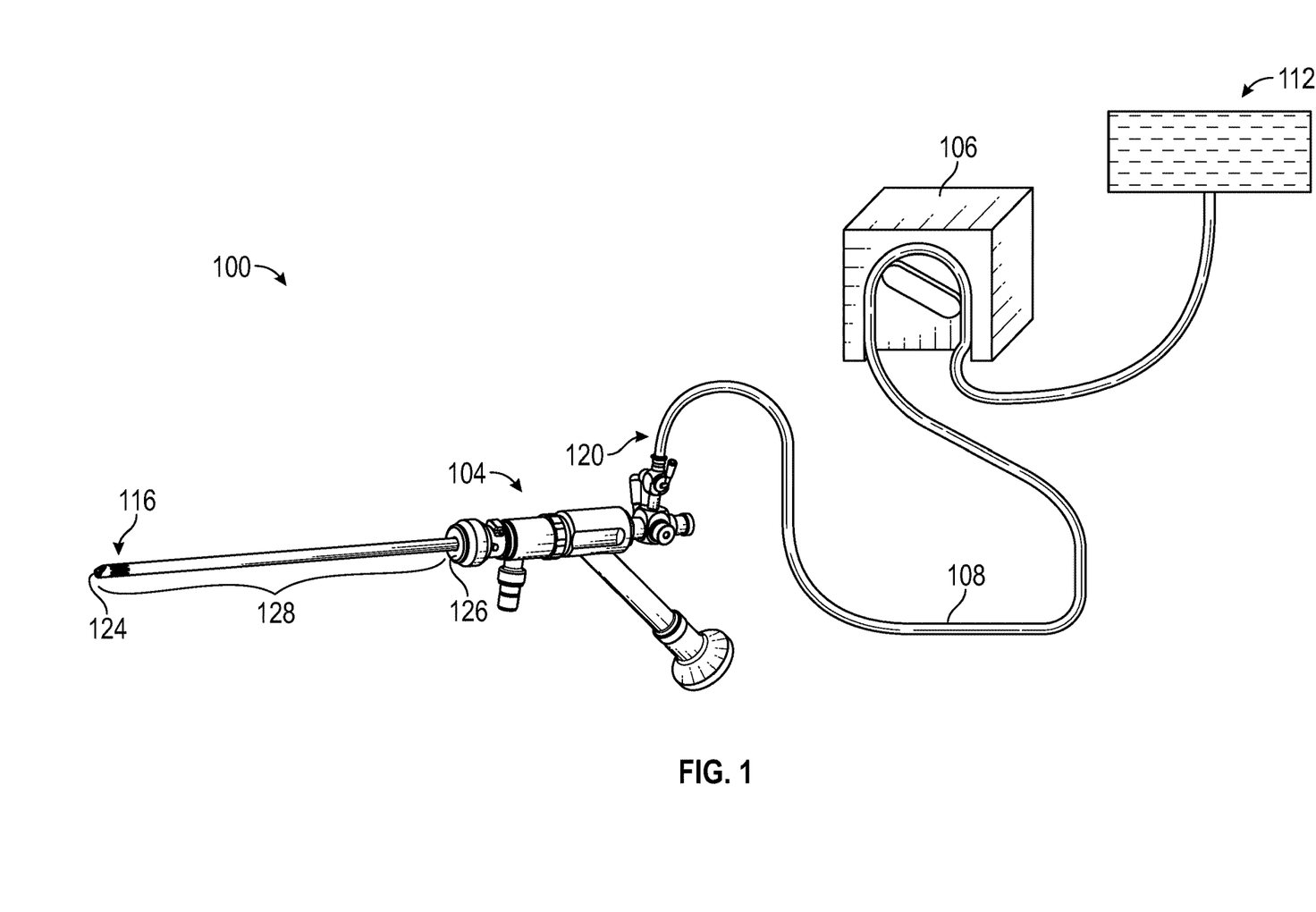
FIG. 1 shows an endoscopic system in accordance with the present disclosure.

FIG. 1 shows an example endoscopic system 100 that includes an endoscopic device 104 including an elongated shaft 128 extending between a proximal end 126 and a distal end 124 of the endoscopic device 104. In the example, the endoscopic device 104 is connected to a fluid pump 106 and a fluid reservoir 112 (such as a saline bag) by way of a fluid line 108 that is coupled to a fluid port 120. The fluid pump 106 may be fluidly coupled to a separate fluid reservoir 112, or alternatively the fluid pump 106 may include a fluid reservoir. The fluid pump 106 may be a peristaltic pump, a positive displacement pump, or a centrifugal pump, any of which may be employed to generate fluid inflow (e.g., via negative pressure). Alternatively, the fluid pump 106 may be omitted and the fluid reservoir 112 may be in direct fluid communication with the fluid port 120, e.g., to provide fluid inflow via gravity. The endoscopic device 104 may further include optics, e.g., lenses and/or image capture electronics, together with an illumination source to enable visualization of a field of view emanating from distal end 124. The endoscopic device 104 may additionally or alternatively include a working channel to enable insertion of a working instrument, e.g., a resection device, through the endoscope 104 and into a surgical site. Alternatively, the endoscopic device 104 may itself be a working instrument.

In a hysteroscopy procedure, for example, the distal end 124 of endoscopic device 104 is inserted transvaginally through a patient's cervix and into the patient's uterus. The patient's cervix may expand circumferentially to accommodate the endoscopic device 104, and effectively create a seal about the endoscopic device 104. During a hysteroscopy, fluid (e.g., pressurized fluid) may leak from the uterus 311 (or uterus 411 in FIG. 4) through the cervix (see, e.g., cervix 313 in FIG. 3 or cervix 413 in FIG. 4) to a patient's vaginal area. Leaking fluid may be collected in an under-buttocks drape, which is positioned between the patient's legs. However, the drape's function depends on correct placement of the drape throughout the procedure, and thus fluid often escapes capture.

Figure 2:
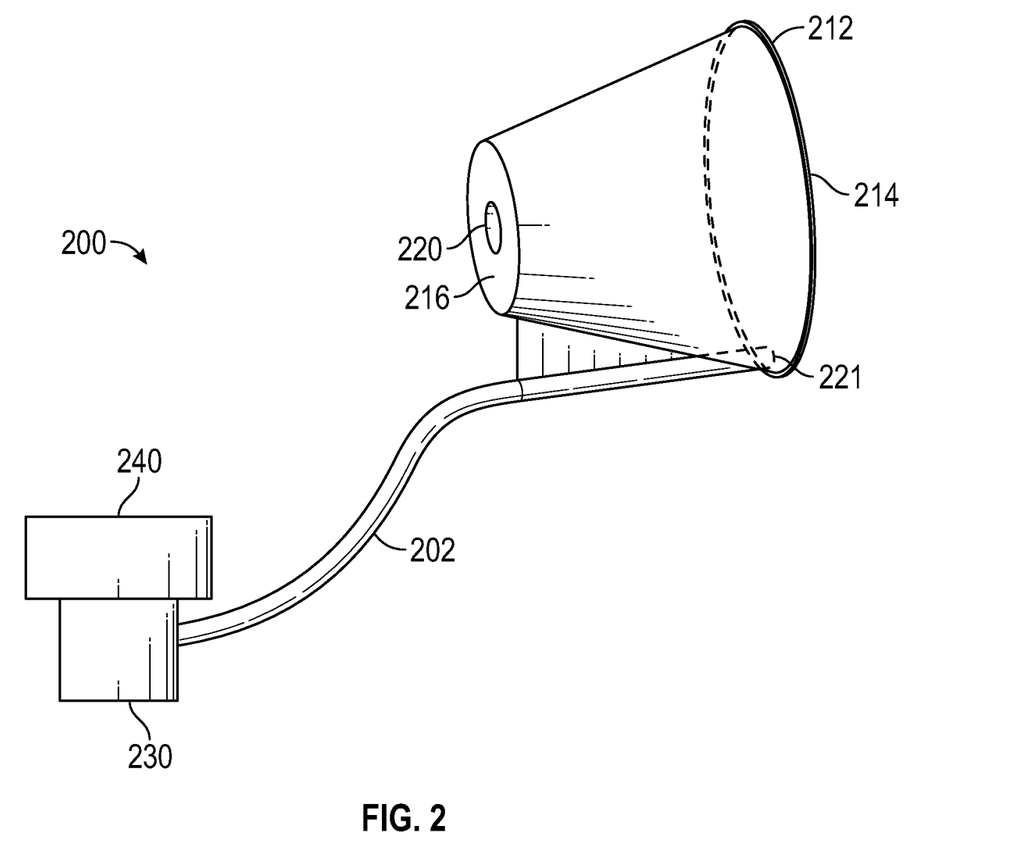
FIG. 2 is a side view of a fluid collecting sheath in accordance with the present disclosure.
Figure 3:
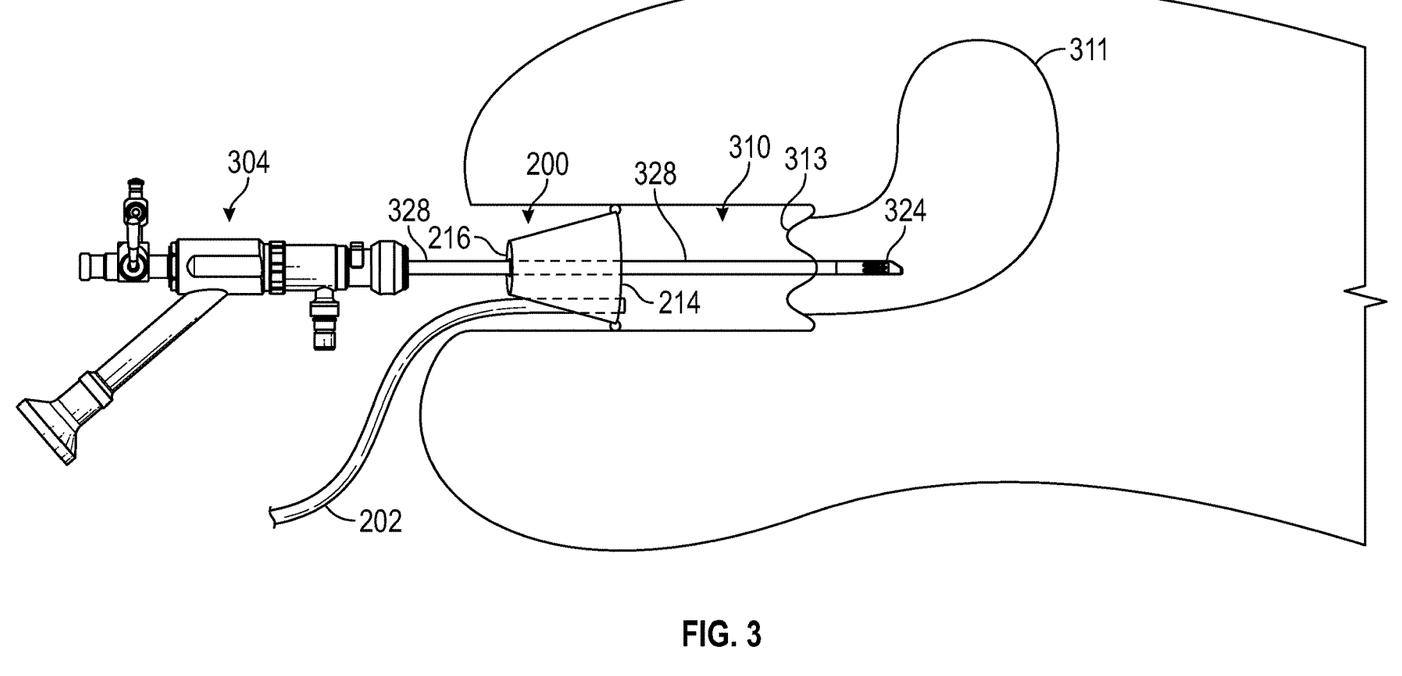
FIG. 3 illustrates the fluid collecting sheath of FIG. 2 positioned between vaginal walls of a patient with the endoscope of FIG. 1 extending through the fluid collecting sheath.

FIGS. 2 and 3 show a fluid collecting sheath 200 in accordance with one aspect of the present disclosure. An endoscopic instrument, e.g., endoscope 304, extends through a proximal orifice 220 at a proximal end 216 of the fluid collecting sheath 200 such that a distal end 324 of the endoscope 304 extends through a patient's vagina 310 and cervix 314 and into the patient's uterus 311. The endoscope 304 may be substantially the same as the endoscopic device 104 described with reference to FIG. 1.

A fluid line 202 extends from a distal end 214 of the fluid collecting sheath 200. The fluid line 202 forms a fluid drain 221 at the distal end 214 of the fluid collecting sheath 200. The fluid drain 221 is configured to drain fluid leaking through the patient's cervix 313 and passed into the patient's vagina 310. The suction or drain line 202 may be in fluid communication with a collection vessel 230. A vacuum source 240 may create negative pressure in the fluid line 202 to draw fluid into the fluid drain 221 or the fluid line 202 may transport fluid from the fluid collection sheath 200 to the collection vessel 230 under gravity.

An outer edge 212 of the fluid collecting sheath 200 is flexible to conform to and create a seal against walls of a patient's vagina 310 and, in some cases, about the cervix 313. The outer edge 212 is collapsible for insertion into the vagina 310. The outer edge 212 of the fluid collecting sheath 200 may act as a vaginal retractor to allow visualization of the patient's cervix 313 through the proximal orifice 220. The fluid collecting sheath 200 may taper in diameter in a distal-to-proximal direction.

The proximal orifice 220 may be flexible to expand and contract to various diameters to receive various sized elongated shafts 328 therein. The proximal orifice 220 may be dimensioned such that the endoscope 304 can move independently of the fluid collecting sheath 200. Alternatively, the fluid collecting sheath 200 may be removable, but securely fixed to the elongated shaft 328 of the endoscope 304, e.g., under resilient and/or friction fit engagement.

Figure 4:
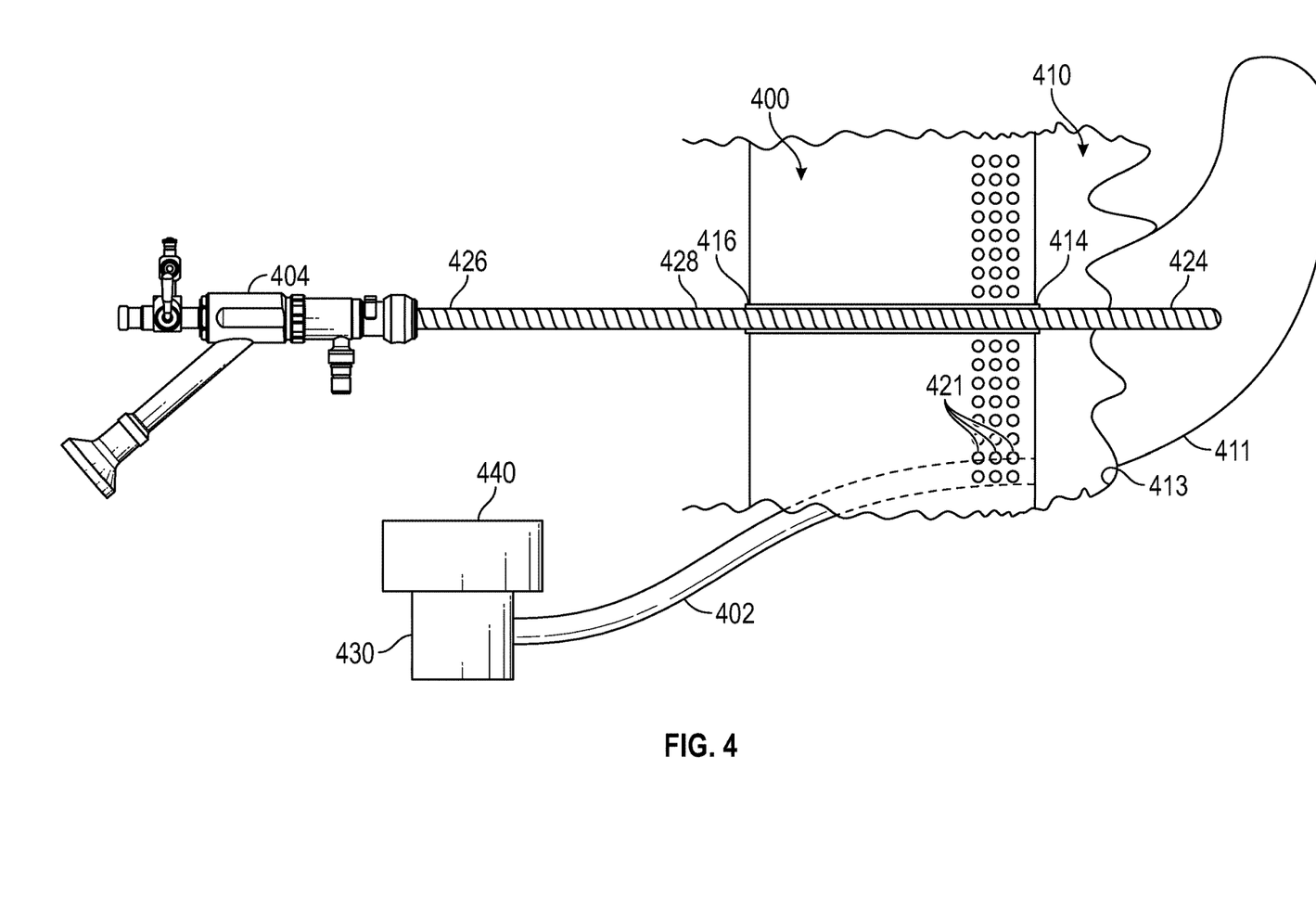
FIG. 4 is a top plan view of another fluid collecting sheath in accordance with the present disclosure positioned between vaginal walls of a patient.
Figure 5:
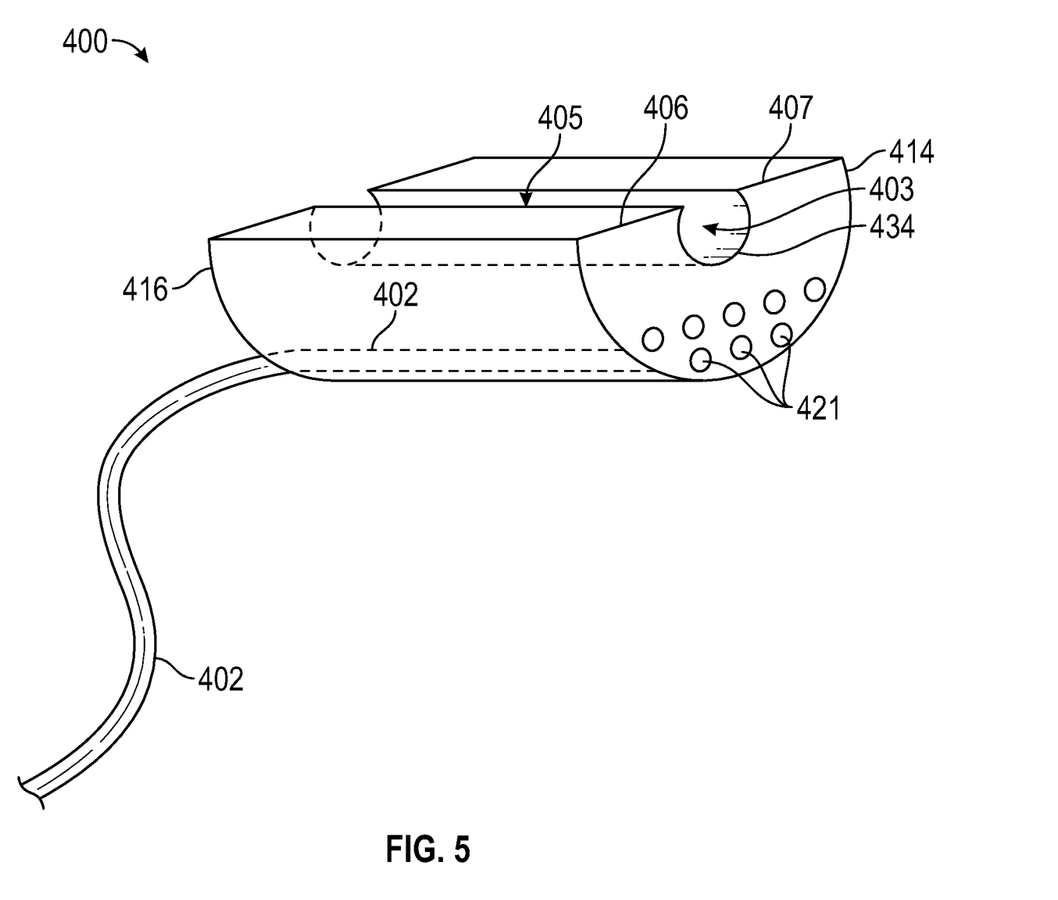
FIG. 5 is a perspective view of the fluid collecting sheath of FIG. 4.
Figure 6:
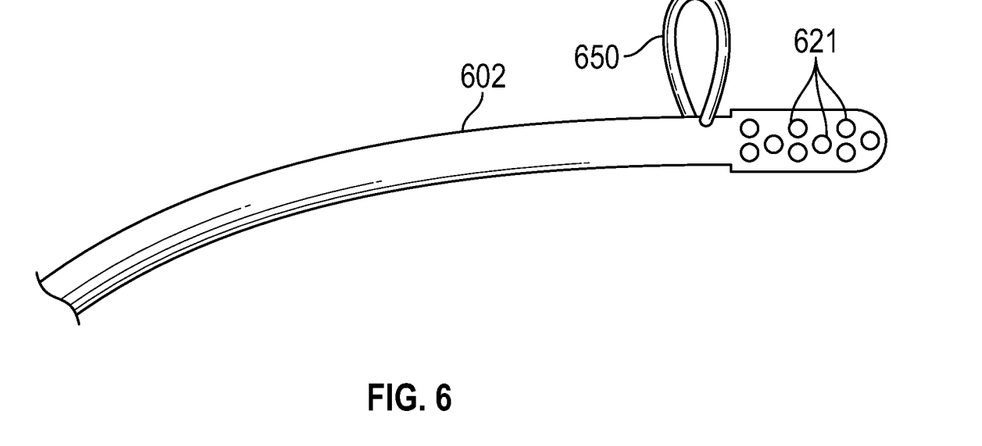
FIG. 6 is a side view of a fluid line having a collar in accordance with the present disclosure.

FIGS. 4 to 6 show a surgical system including a fluid collecting sheath 400 in accordance with one aspect of the present disclosure. The system includes an endoscope 404 defining a proximal end 426, a distal end 424 and an elongated shaft 428 extending between the proximal end 426 and the distal end 424 of the endoscope 404. The endoscope 404 may be substantially the same as the endoscopic device 104 described with reference to FIG. 1.

The fluid collecting sheath 400 defines a proximal end 416 and a distal end 414. The fluid collecting sheath 400 is configured for insertion into a vaginal opening 410. In use, the fluid collecting sheath 400 is inserted distal end 414 first. The fluid collecting sheath 400 includes fluid collecting apertures 421 defined at the distal end 414 of the fluid collecting sheath 400. A single fluid collecting aperture 421 or a plurality of fluid collecting apertures 421 may be defined at the distal end 414 of the fluid collecting sheath 400. A fluid line 402 is in fluid communication with the fluid collecting apertures 421. The fluid collecting apertures 421 are each positioned at a lower portion of the fluid collecting sheath 400 such that gravity directs fluid toward the fluid collecting apertures 421.

The fluid collecting apertures 421 may be positioned at a side of the fluid collecting sheath 400 substantially opposite from channel 403. As an example, the fluid collecting apertures 421 may be positioned at a lower portion of the fluid collecting sheath 400 such that gravity directs fluids toward the fluid collecting apertures 421. Fluid may additionally be pulled toward and drawn into the fluid collecting apertures 421 through negative pressure created in the fluid line 402 (e.g., by vacuum source 440).

A channel 403 is formed in the fluid collecting sheath 400. The channel 403 defines a substantially circular cross-sectional shape. The channel 403 extends between the proximal end 416 and the distal end 414 of the fluid collecting sheath 400. The channel 403 defines an elongated opening 405 therein along the length thereof. The opening 405 may be formed at an outer edge (e.g., an upper portion) of the fluid collecting sheath 400. The opening 405 is configured to allow the elongated shaft 428 of the endoscope 404 to pass transversely therethrough. The channel 403 of the fluid collecting sheath 400 is configured to operably engage the elongated shaft 428 of the endoscope 404 by passing the elongated shaft 428 of the endoscope 404 transversely through the opening 405 of the channel 403. Radial inward pressure may be applied to the elongated shaft 428 by the sidewalls defining the channel 403.

The channel 403 of the fluid collecting sheath 400 fixedly engages the elongated shaft 428 of the endoscope 404. The fluid collecting sheath 400 and the endoscope 404 move substantially in concert with one another. For example, advancing the endoscope 404 to distally advance the distal end 424 of the elongated shaft 428 will result in a corresponding distal advancement of the fluid collecting sheath 400. Alternatively, the fluid collecting sheath 400 may be configured to enable the endoscope 404 to move independently of the fluid collecting sheath 400.

The channel 403 is configured to selectively expand in width to accommodate and operatively connect with elongated shafts of endoscopes having various widths or diameters.

At least one drip flange (e.g., drip flanges 406 and/or 407) may be formed at the distal end 414 of the fluid collecting sheath 400. The at least one drip flange directs fluid away from the channel 403 of the fluid collecting sheath 400. For example, the at least one drip flange may be distally extending lip extending distally from the distal end 414 of the fluid collecting sheath 400. The distally extending lip including drip flanges 406 and 407 may extend distally around a distal end 434 of the channel 403, thus directing water away from the channel 403 and toward the fluid collecting apertures 421.

A collection vessel 430 is in fluid communication with the fluid line 402. The collection vessel 430 receives fluid captured by the fluid collecting apertures 421 after the captured fluid has passed through the fluid line 402.

The fluid collecting sheath 400 and the fluid line 402 may be a single integrally formed structure in which the fluid line 402 extends within the fluid collecting sheath 400 between the proximal end 416 and the distal end 414 of the fluid collecting sheath (see, e.g., FIG. 5).

A vacuum source 440 may be in fluid communication with the fluid line 402. The vacuum source 440 may be connected with the collection vessel 430 to apply negative pressure to the fluid line 402 therethrough (see, e.g., FIG. 4). Alternatively, the vacuum source 440 may be connected directly with the fluid line 403. The vacuum source 440 applies negative pressure to the fluid collecting apertures 421 via the fluid line 402 to draw fluid into and through the fluid line 402. The vacuum source 440 may in some embodiments be a peristaltic pump, a positive displacement pump, or a centrifugal pump, any of which may be employed to generate fluid inflow (e.g., via negative pressure). Alternatively, fluid may be transported through fluid line 402 under gravity.

According to one aspect of the disclosure, the fluid collecting sheath 400 can be removably coupled to the endoscope 404. For example, in use, the endoscope 404 may be inserted into a vaginal opening 410 prior to the insertion of the fluid collecting sheath 400. Subsequently, the fluid collecting sheath 400 may be inserted into the vaginal opening 410 and then removably coupled to the elongated shaft 428 of the endoscope 404 to secure the fluid collecting sheath 400 to the endoscope 404 without the need to remove the endoscope 404. This may be achieved by applying pressure to the fluid collecting sheath 400 to force the elongated shaft 428 of the endoscope 404 transversely into the channel 403 through opening 405. The fluid collecting sheath 400 may include or be formed of a material (e.g., a flexible polymer) allowing sufficient bending to allow opening 405 to open sufficiently to allow elongated shaft 428 of the endoscope 404 to be securely forced into channel 403. Thus, during use the fluid collecting sheath 400 may remain substantially fixed to the endoscope 404. The fluid collecting sheath 400 may also be decoupled from the elongated shaft 428 of the endoscope 404 and removed without the need to remove the endoscope 404 by reversing the attachment steps described above. Thus, the fluid collecting sheath 400 may be introduced or removed as needed without the need to also remove the endoscope 404.

Referring particularly to FIG. 6, a collar 650 extends from a fluid line 602. The fluid line 602 may be substantially the same as fluid line 402 described herein (FIG. 4). The collar 650 is configured to be secured to an endoscope (e.g., to an elongated shaft 428 of endoscope 404 (FIG. 4)). The collar 650 may be at least partially elastic. The fluid line 602 may connect with fluid collecting apertures 621. Fluid collecting apertures 621 may be substantially the same as fluid collecting apertures 421 described herein (see FIG. 4).

Figure 7:
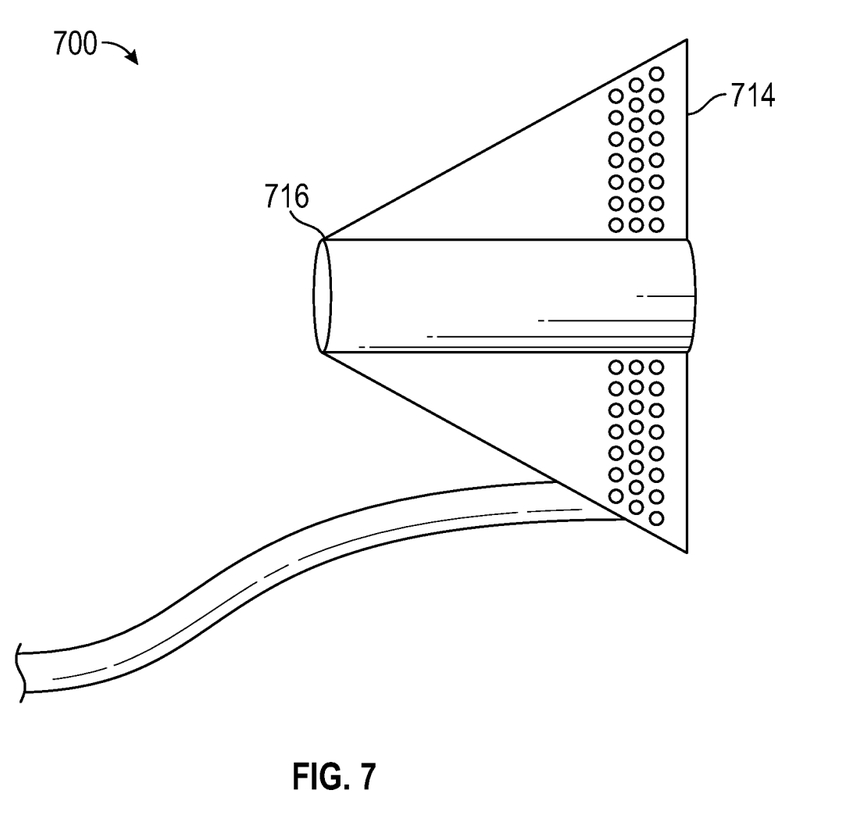
FIG. 7 is a top plan view of another fluid collecting sheath in accordance with the present disclosure.

FIG. 7 shows a fluid collecting sheath 700 having a proximal end 716 and a distal end 714. Fluid collecting sheath 700 may be substantially the same as fluid collecting sheath 400 described herein, except that fluid collecting sheath 700 may have a tapered proximal end 716. For example, a width of the fluid collecting sheath 700 when viewed from a top plan view may narrow gradually from the distal end 714 to the proximal end 716. The tapered distal end 716 may allow for easier grasping by a surgical instrument to remove fluid collecting sheath 700 from a vaginal opening.

The various endoscopic systems disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the endoscopic system s described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system, comprising
an endoscope defining a proximal end, a distal end and an elongated shaft extending between the proximal end and the distal end of the endoscope;
a fluid collecting sheath defining a proximal end and a distal end, the fluid collecting sheath configured for insertion into a vaginal opening, wherein the fluid collecting sheath includes:
a plurality of distal-facing fluid collecting apertures defined at the distal end of the fluid collecting sheath;
a fluid line in fluid communication with the plurality of distal-facing fluid collecting apertures; and
a channel formed in the fluid collecting sheath, the channel extending between the proximal end and the distal end of the fluid collecting sheath, the channel defining an opening,
wherein the channel of the fluid collecting sheath is configured to operably engage the elongated shaft of the endoscope within the channel by passing the elongated shaft of the endoscope transversely through the opening of the channel.

2. The system of claim 1, wherein the channel of the fluid collecting sheath is configured to fixedly engage the elongated shaft of the endoscope therein, such that the fluid collecting sheath and the endoscope move in concert with one another.

3. The system of claim 1, further including at least one drip flange formed at the distal end of the fluid collecting sheath, the at least one drip flange configured to direct fluid away from the channel of the fluid collecting sheath.

4. The system of claim 1, further including a collection vessel in fluid communication with the fluid line, the collection vessel configured to receive fluid captured by the plurality of distal-facing fluid collecting apertures.

5. The system of claim 1, further including a collar extending from the fluid line, the collar configured to be secured to the endoscope.

6. The system of claim 5, wherein the collar is at least partially elastic.

7. The system of claim 1, wherein the fluid collecting sheath and the fluid line are a single integrally formed structure in which the fluid line extends within the fluid collecting sheath between the proximal end and the distal end of the fluid collecting sheath.

8. The system of claim 1, wherein the opening of the channel is formed through an outer edge of the fluid collecting sheath.

9. The system of claim 1, wherein the channel is configured to selectively expand in width.

10. The system of claim 1, further including a vacuum source in fluid communication with the fluid line, the vacuum source configured to apply negative pressure to the plurality of distal-facing fluid collecting apertures to draw fluid through the fluid line.

11. A fluid collecting sheath defining a proximal end and a distal end, the fluid collecting sheath configured for insertion into a vaginal opening, wherein the fluid collecting sheath includes:
a plurality of distal-facing fluid collecting apertures defined at the distal end of the fluid collecting sheath;
a fluid line in fluid communication with the plurality of distal-facing fluid collecting apertures; and
a channel formed in the fluid collecting sheath, the channel extending between the proximal end and the distal end of the fluid collecting sheath, the channel defining an opening therein,
wherein the channel of the fluid collecting sheath is configured to operably engage an elongated shaft of an endoscope within the channel by passing the elongated shaft of the endoscope transversely through the opening of the channel.

12. The fluid collecting sheath of claim 11, wherein the channel of the fluid collecting sheath is configured to fixedly engage the elongated shaft of the endoscope therein, such that the fluid collecting sheath and the endoscope move in concert with one another.

13. The fluid collecting sheath of claim 11, further including at least one drip flange formed at the distal end of the fluid collecting sheath, the at least one drip flange configured to direct fluid away from the channel of the fluid collecting sheath.

14. The fluid collecting sheath of claim 11, further including a collection vessel in fluid communication with the fluid line, the collection vessel configured to receive fluid captured by the plurality of distal-facing fluid collecting apertures.

15. The fluid collecting sheath of claim 11, further including a collar extending from the fluid line, the collar configured to be secured to the endoscope.

16. The fluid collecting sheath of claim 15, wherein the collar is at least partially elastic.

17. The fluid collecting sheath of claim 11, wherein the fluid collecting sheath and the fluid line are a single integrally formed structure in which the fluid line extends within the fluid collecting sheath between the proximal end and the distal end of the fluid collecting sheath.

18. The fluid collecting sheath of claim 11, wherein the opening of the channel is formed through an outer edge of the fluid collecting sheath.

19. The fluid collecting sheath of claim 11, wherein the channel is configured to selectively expand in width.

20. A system, comprising
an endoscope defining a proximal end, a distal end and an elongated shaft extending between the proximal end and the distal end of the endoscope;
a fluid collecting sheath defining a proximal end and a distal end, the fluid collecting sheath configured for insertion into a vaginal opening, wherein the fluid collecting sheath includes:
a distal-facing fluid collecting aperture defined at the distal end of the fluid collecting sheath;
a fluid line in fluid communication with the distal-facing fluid collecting aperture; and
a channel formed in the fluid collecting sheath, the channel extending between the proximal end and the distal end of the fluid collecting sheath, the channel defining an opening therein,
wherein the channel of the fluid collecting sheath is configured to operably engage the elongated shaft of the endoscope within the channel by passing the elongated shaft of the endoscope transversely through the opening of the channel.

\* \* \* \* \*